US010143361B2

(12) United States Patent
Inoue

(10) Patent No.: US 10,143,361 B2
(45) Date of Patent: Dec. 4, 2018

(54) ENDOSCOPE SYSTEM HAVING ROTATABLE ELONGATED PART AND BENDING PART CONTROLLED TO BEND BASED ON ROTATION OF ELONGATED PART

(71) Applicant: OLYMPUS CORPORATION, Tokyo (JP)

(72) Inventor: Shintaro Inoue, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 15/418,929

(22) Filed: Jan. 30, 2017

(65) Prior Publication Data
US 2017/0135557 A1    May 18, 2017

Related U.S. Application Data

(63) Continuation of application No. PCT/JP2015/083720, filed on Dec. 1, 2015.

(30) Foreign Application Priority Data

Dec. 19, 2014  (JP) ................................ 2014-257192

(51) Int. Cl.
*A61B 1/005*    (2006.01)
*A61B 1/05*    (2006.01)
(Continued)

(52) U.S. Cl.
CPC ........ *A61B 1/0052* (2013.01); *A61B 1/00006* (2013.01); *A61B 1/0008* (2013.01);
(Continued)

(58) Field of Classification Search
CPC ......... A61B 1/0052; A61B 1/045; A61B 1/05; A61B 1/00006; A61B 1/00009; A61B 1/051; H04N 5/2259
(Continued)

(56) References Cited

U.S. PATENT DOCUMENTS

| | | | |
|---|---|---|---|
| 5,184,601 A * | 2/1993 | Putman | B25J 9/042 312/209 |
| 6,036,637 A | 3/2000 | Kudo | |

(Continued)

FOREIGN PATENT DOCUMENTS

| | | |
|---|---|---|
| CN | 1925779 A | 3/2007 |
| CN | 102438795 A | 5/2012 |

(Continued)

OTHER PUBLICATIONS

Chinese Office Action dated Sep. 13, 2017 in Chinese Patent Application No. 201580041768.6.

(Continued)

*Primary Examiner* — John P Leubecker
(74) *Attorney, Agent, or Firm* — Scully, Scott, Murphy & Presser, P.C.

(57) ABSTRACT

An endoscope system is provided with an operation part, an elongated part, an imaging part, a control part, a display part, a rotation operation input part, and a rotation coupling part that rotates an imaging field of view in the imaging part around the optical axis in accordance with the rotation amount provided to the control part, wherein the control part outputs to the display part an image which has been captured by the imaging part and is brought into a state in which the field of view is rotated by the rotation coupling part.

8 Claims, 11 Drawing Sheets

(51) Int. Cl.
*A61B 1/045* (2006.01)
*A61B 1/00* (2006.01)
*G02B 23/24* (2006.01)

(52) U.S. Cl.
CPC .......... *A61B 1/00149* (2013.01); *A61B 1/045* (2013.01); *A61B 1/05* (2013.01); *A61B 1/051* (2013.01); *G02B 23/2476* (2013.01); *A61B 1/00039* (2013.01)

(58) Field of Classification Search
USPC ....................................................... 600/137
See application file for complete search history.

(56) References Cited

U.S. PATENT DOCUMENTS

| | | | | |
|---|---|---|---|---|
| 6,464,631 | B1* | 10/2002 | Girke | A61B 1/05 600/109 |
| 6,695,774 | B2* | 2/2004 | Hale | A61B 1/00039 356/241.3 |
| 7,713,189 | B2* | 5/2010 | Hanke | A61B 1/00183 600/109 |
| 2002/0095146 | A1* | 7/2002 | Hutchins | A61B 18/1492 606/39 |
| 2004/0267090 | A1 | 12/2004 | Ueno et al. | |
| 2005/0228230 | A1* | 10/2005 | Schara | A61B 1/00045 600/171 |
| 2007/0030344 | A1* | 2/2007 | Miyamoto | A61B 1/00045 348/65 |
| 2009/0054733 | A1* | 2/2009 | Marescaux | A61B 17/29 600/141 |
| 2010/0022825 | A1* | 1/2010 | Yoshie | A61B 1/00133 600/104 |
| 2010/0125166 | A1* | 5/2010 | Henzler | A61B 1/00177 600/109 |
| 2013/0165908 | A1* | 6/2013 | Purdy | A61F 5/0013 606/1 |
| 2014/0066710 | A1* | 3/2014 | Graves | A61B 1/00066 600/109 |
| 2014/0221749 | A1* | 8/2014 | Grant | A61B 1/00183 600/112 |
| 2014/0357947 | A1* | 12/2014 | Fujitani | A61B 1/00096 600/104 |
| 2014/0357952 | A1* | 12/2014 | Krohn | A61B 1/00183 600/112 |
| 2015/0265807 | A1* | 9/2015 | Park | A61M 25/0133 600/424 |
| 2015/0359420 | A1* | 12/2015 | Hatase | A61B 1/051 600/110 |
| 2016/0338789 | A1* | 11/2016 | De Mathelin | A61B 34/30 |

FOREIGN PATENT DOCUMENTS

| | | |
|---|---|---|
| JP | H02-239833 A | 9/1990 |
| JP | H06-237881 A | 8/1994 |
| JP | 2000-180735 A | 6/2000 |
| JP | 2005-7148 A | 1/2005 |
| JP | 2006-212357 A | 8/2006 |
| JP | 3831273 B2 | 10/2006 |
| JP | 2010-069108 A | 4/2010 |
| JP | 2012-029822 A | 2/2012 |
| JP | 5583860 B2 | 9/2014 |

OTHER PUBLICATIONS

International Search Report dated Feb. 16, 2016 issued in PCT/JP2015/083720.
Extended Supplementary European Search Report dated Aug. 13, 2018 in European Patent Application No. 15 86 9785.4.

* cited by examiner

ENDOSCOPE SYSTEM HAVING ROTATABLE ELONGATED PART AND BENDING PART CONTROLLED TO BEND BASED ON ROTATION OF ELONGATED PART

CROSS REFERENCE TO RELATED APPLICATIONS

This application is a continuation application based on a PCT Patent Application No. PCT/JP2015/083720, filed on Dec. 1, 2015, whose priority is claimed on Japanese Patent Application No. 2014-257192, filed Dec. 19, 2014, the entire content of which are hereby incorporated by reference.

BACKGROUND OF THE INVENTION

Technical Field

The present invention relates to an endoscope system.

Description of the Related Art

Endoscope systems are known for imaging a site in a body to be observed or treated. For example, Japanese Patent (Granted) Publication No. 5583860 and Japanese Unexamined Patent Application, First Publication No. 2012-29822 disclose technologies in which a vicinity of a distal end of an insertion part can be bent actively.

When an observation is performed using an endoscope system, there is a case in which an image of an observed object to be captured is made to be rotated. As a technique for rotating the image of an observed object, for example, Japanese Patent (Granted) Publication No. 3831273 discloses an electronic endoscope including an insertion part having a flexible tubular member mounted inside with an imaging element. When rotating the tubular member of the electronic endoscope disclosed in Japanese Patent (Granted) Publication No. 3831273, it is possible to rotate the element of the imaging part even when the insertion part of the endoscope is in a bending state.

SUMMARY

According to an aspect of the present invention, an endoscope system includes: an operation part; an elongated part connected to the operation part; an imaging part disposed at a distal part of the elongated part and configured to capture an image of an observation target object; a control part configured to acquire the image from the imaging part; a display part connected to the control part and configured to display the image captured by the imaging part; a rotation operation input part provided at the operation part so as to be graspable by an operator and capable of performing a relative rotation with respect to the elongated part, and configured to output an amount of the relative rotation to the control part as a rotation amount of the imaging part with respect to the image around an optical axis of the imaging part; and a field-of-view rotating part configured to rotate an imaging field of view in the imaging part around the optical axis in accordance with the rotation amount provided to the control part. The control part outputs to the display part an image captured by the imaging part and brought into a state in which the field of view is rotated by the field-of-view rotating part.

According to an aspect of the present invention, the endoscope system may further include: an active bending part connected to a distal end of the elongated part and capable of performing a bending motion; and a bending operation input part disposed at the rotation operation input part and configured to output a bending amount of the active bending part to the control part. The imaging part may be connected to a distal end of the active bending part. By the control part changing the bending amount provided from the bending operation input part in accordance with the rotation amount, the control part may specify a bending direction of the active bending part so as to offset the rotation of the imaging field of view by being shifted by the rotation amount from a direction of input to the bending operation input part.

According to an aspect of the present invention, the endoscope system may further include: a switching part configured to switch between a state in which it is possible to perform the relative rotation of the rotation operation input part with respect to the elongated part and a state in which it is impossible to perform the relative rotation.

According to an aspect of the present invention, the endoscope system may further include: a supporting arm configured to hold the elongated part; a stopper part provided on the supporting arm so as to restrict the elongated part rotating with respect to the supporting arm around a longitudinal axis of the elongated part as a rotation center; and a mode change input part connected to the stopper part so as to switch between a mode of fixing the elongated part to the supporting arm by the stopper part and a mode in which the fixing is released.

According to an aspect of the present invention, in the endoscope system, the bending operation input part may include: an input device configured to receive an operation for changing the bending amount and output the bending amount of the active bending part to the control part; and a feedback mechanism configured to feed back to the input device a deviation from a direction of input to the input device caused in accordance with the rotation amount.

According to an aspect of the present invention, in the endoscope system, the field-of-view rotating part may be provided in the imaging part and may be a rotation coupling part configured to rotate the imaging part relative to the elongated part in accordance with the rotation amount supplied from the rotation operation input part.

According to an aspect of the present invention, in the endoscope system, the field-of-view rotating part may include a rotation amount detection part configured to detect an amount of a relative rotation of the rotation operation input part with respect to the elongated part, and may be configured to rotate the imaging field of view in the imaging part around the optical axis based on a detection result by the rotation amount detection part.

DETAILED DESCRIPTION OF THE PREFERRED EMBODIMENTS

First Embodiment

Figure 1:
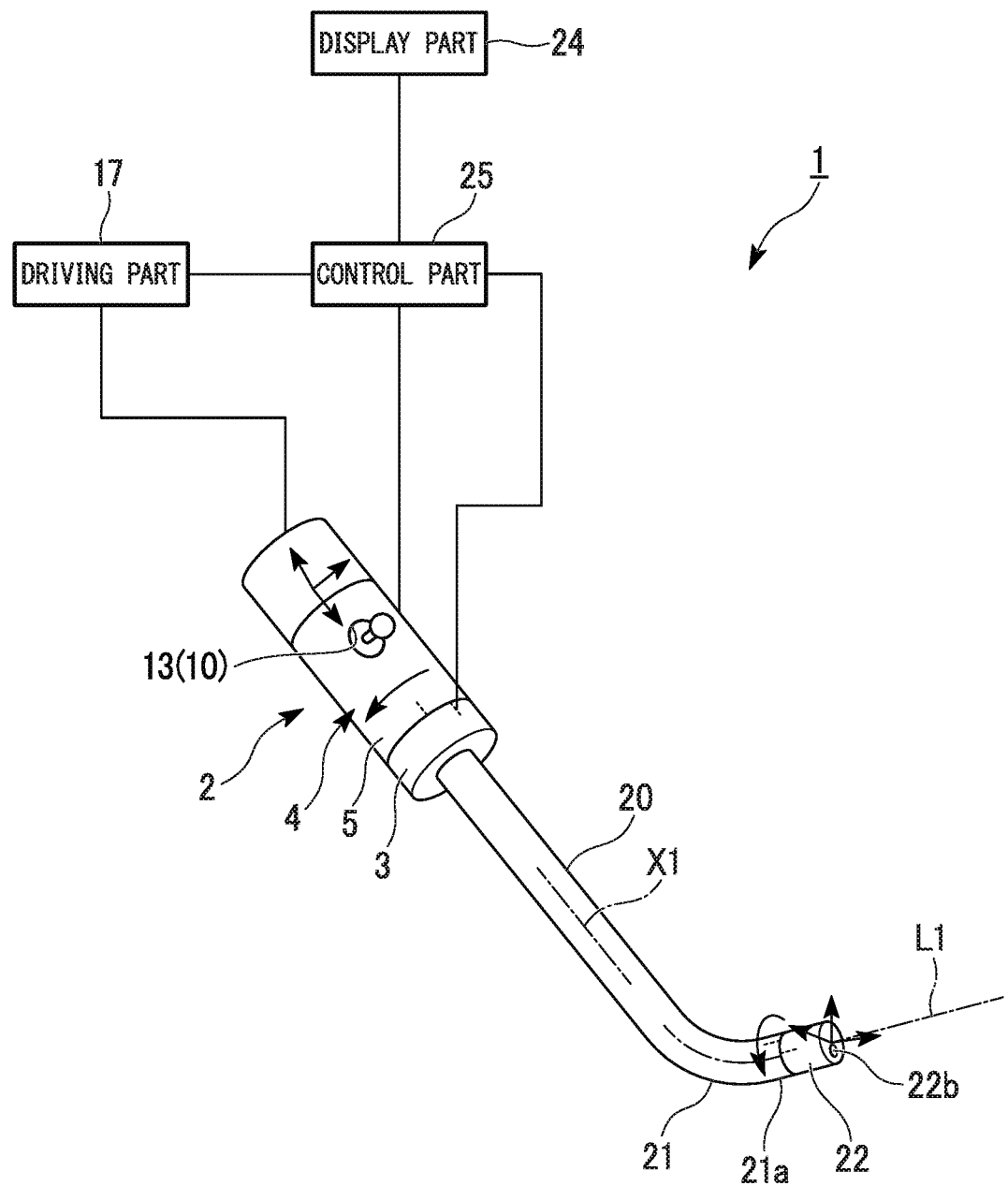
FIG. 1 is an overall view of an endoscope system according to a first embodiment of the present invention.
Figure 2:
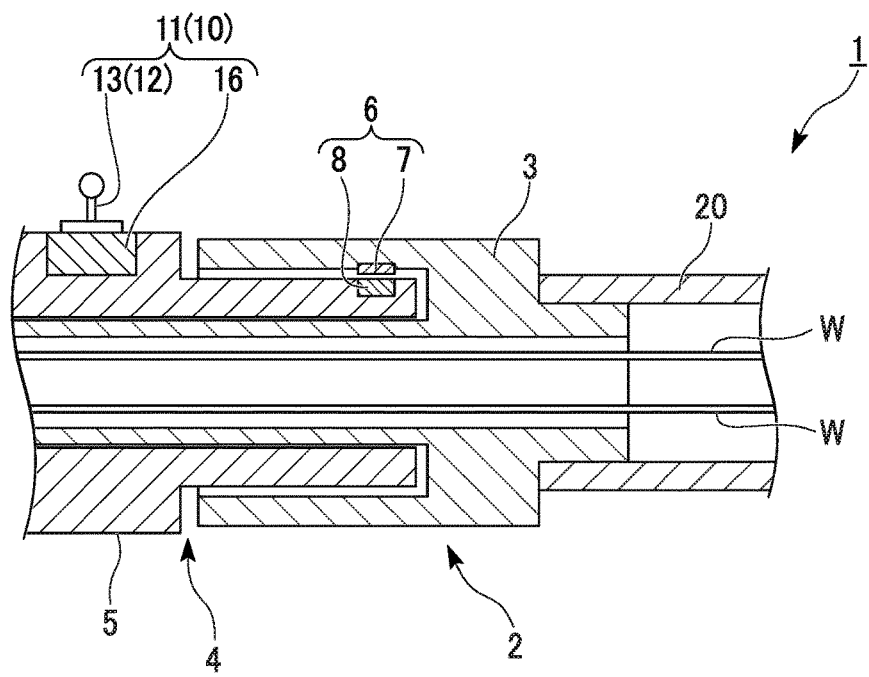
FIG. 2 is a cross sectional view of a part of an operation part of the endoscope system.
Figure 3:
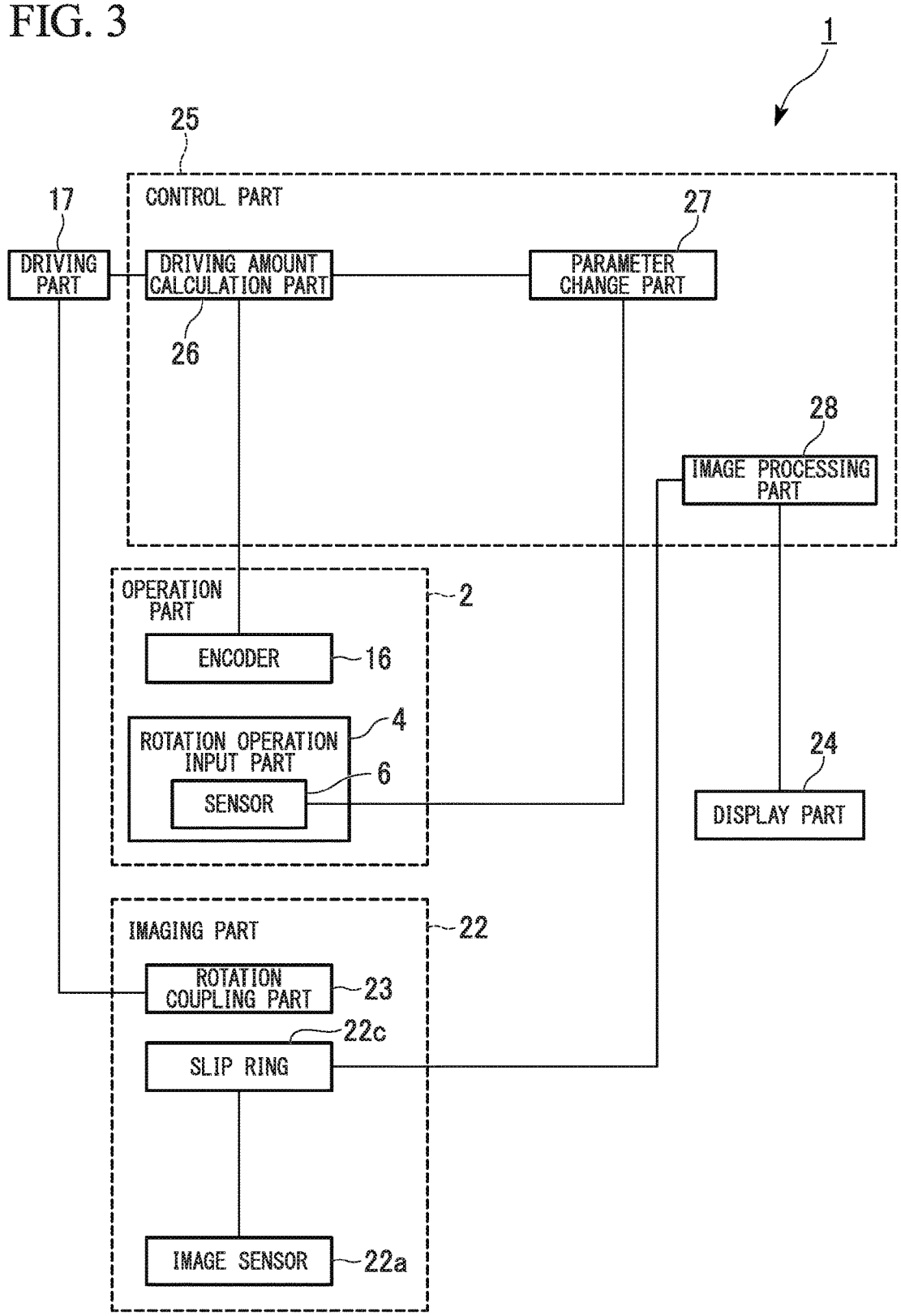
FIG. 3 is a block diagram of the endoscope system.
Figure 4:
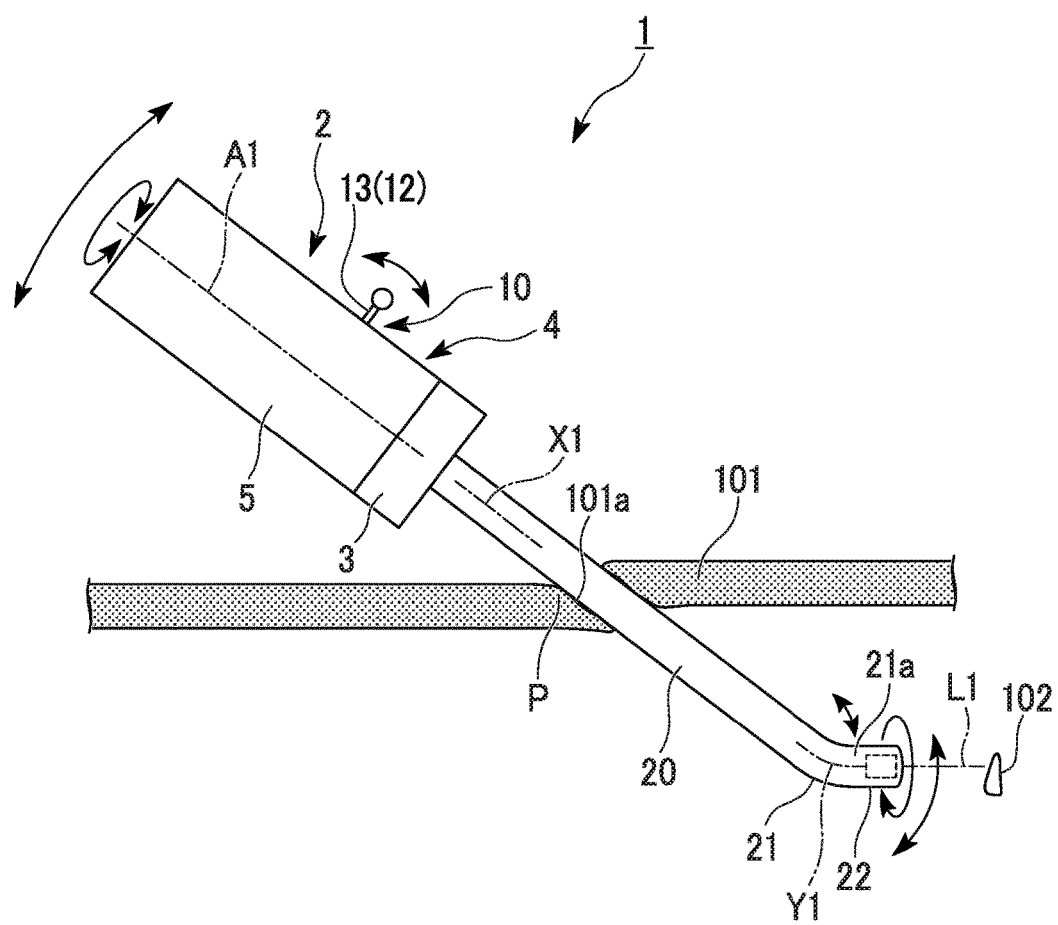
FIG. 4 is a diagram for describing an operation of the endoscope system.
Figure 5A:
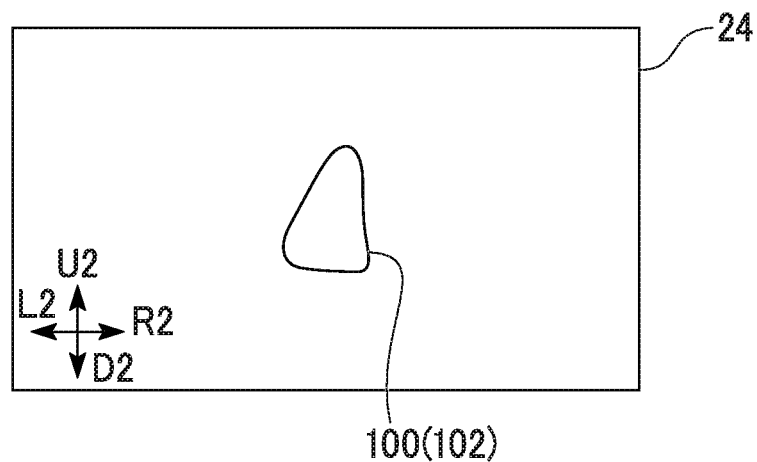
FIG. 5A is a schematic view showing an example of operating the endoscope system while viewing an image captured by the endoscope system.
Figure 5B:
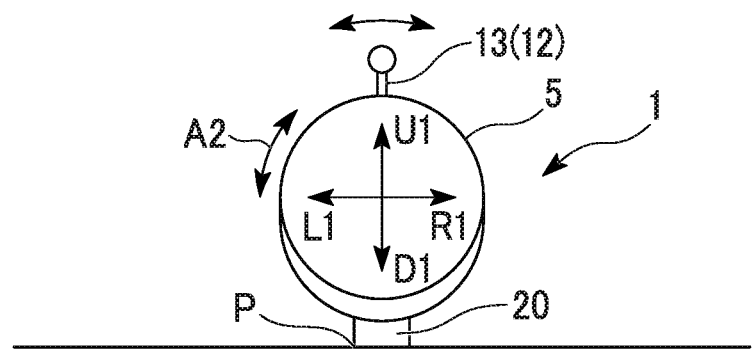
FIG. 5B is a schematic view showing an example of operating the endoscope system while viewing an image captured by the endoscope system.
Figure 6A:
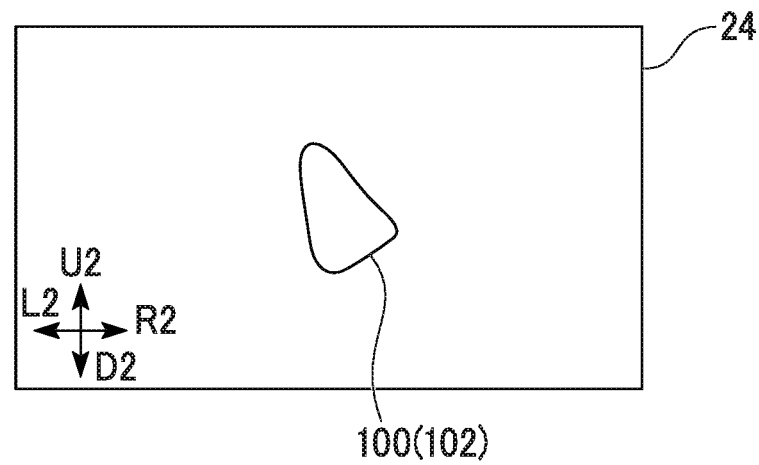
FIG. 6A is a schematic view showing an example of operating the endoscope system while viewing an image captured by the endoscope system.
Figure 6B:
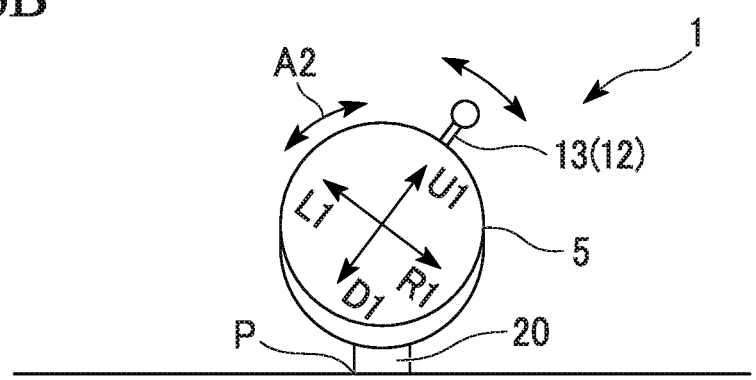
FIG. 6B is a schematic view showing an example of operating the endoscope system while viewing an image captured by the endoscope system.

A first embodiment of the present invention will be described. FIG. 1 is an overall view of an endoscope system of the present embodiment. FIG. 2 is a cross sectional view of a part of an operation part of the endoscope system. FIG. 3 is a block diagram of the endoscope system. FIG. 4 is a diagram for describing an operation of the endoscope system. FIGS. 5A, 5B, 6A and 6B are schematic views showing examples of operating the endoscope system while viewing the image captured by the endoscope system.

As shown in FIGS. 1 and 3, the endoscope system 1 includes an operation part 2, a driving part 17, an elongated part 20, an active bending part 21, an imaging part 22, a display part 24, and a control part 25.

The operation part 2 is disposed at the proximal end of the elongated part 20. The operator using the endoscope system 1 operates the imaging part 22 and the active bending part 21, holding the operation part 2 in hand.

The operation part 2 includes a base part 3, a rotation operation input part 4, and a bending operation input part 10.

As shown in FIGS. 1 and 2, the base part 3 is a cylindrical member at which the proximal end of the elongated part 20 is fixed. Inside the base part 3, a part of a rotation cylinder part 5, which will be described later, of the rotation operation input part 4 is inserted. Further, a marker 7 forming a part of a rotation amount detection part 6, which will be described later, is fixed to the base part 3.

The rotation operation input part 4 is an input part to which an operation for a relative rotation of the imaging part 22 with respect to the active bending part 21 is input.

The rotation operation input part 4 includes a rotation cylinder part 5 and a rotation amount detection part 6.

The rotation cylinder part 5 is a cylindrical member that can be gripped by the operator. The rotation cylinder part 5 is coupled to the base part 3 so as to allow a relative rotation with respect to the elongated part 20. Inside the rotation cylinder part 5, an angle wire W, which will be described later, is inserted. The proximal end of the rotation cylinder part 5 is connected to the driving part 17. Here, in the present embodiment, the driving part 17 may be attached to the proximal end of the rotation cylinder part 5. Further, in the present embodiment, a driving force may be transmitted remotely to the rotation cylinder part 5 using a torque wire and this driving force may be transmitted to the angle wire W.

The rotation amount detection part 6 outputs the amount of the relative rotation of the rotation cylinder part 5 with respect to the elongated part 20 to the control part 25. A rotary encoder, a potentiometer, an acceleration sensor, or the like which are commonly known may be used as the rotation amount detection part 6. In the present embodiment, the rotation amount detection part 6 includes a marker 7 disposed on the base part 3, and a sensor 8 that detects the rotation amount of the rotation cylinder part 5 relative to the base part 3 on the basis of the position of the marker 7 serving as a reference.

The bending operation input part 10 includes an input device 11.

An operation for changing a bending amount of the active bending part 21 is input to the input device 11, thereby, the input device 11 outputs the bending amount of the active bending part 21 to the control part 25. The input device 11 of the bending operation input part 10 includes a movable member 12 disposed in the rotation operation input part 4, and an encoder 16 that detects the amount of movement of the movable member 12.

The movable member 12 of the present embodiment is a joystick 13 that protrudes from the rotation operation input part 4.

The joystick 13 can be bent from a neutral position, corresponding to the bendable direction of the active bending part 21. Upward, downward, left and right are assigned to the joystick 13 so that a direction of a center line A1 (see FIG. 4) of the rotation cylinder part 5 is upward and downward thereof, and a circumferential direction A2 (see FIG. 5B) of the rotation cylinder part 5 is left and right thereof.

When the joystick 13 is bent in a direction of the center line A1 of the rotation cylinder part 5, the active bending part 21 can be bent in a predetermined upward-downward direction of the imaging part 22 (that is, upward-downward direction of the image to be captured by the imaging part 22).

When the joystick 13 is bent in the circumferential direction A2 of the rotation cylinder part 5, the active bending part 21 can be bent in the left-right direction perpendicular to the above upward-downward direction of the imaging part 22 (that is, left-right direction of the image to be captured by the imaging part 22).

The encoder 16 shown in FIGS. 2 and 3 detects the amount of movement or position of the joystick 13 of the bending operation input part 10, and outputs it to the control part 25. That is, the encoder 16 outputs the bending amount (control target value) of the active bending part 21, which is input to the movable member 12, to the control part 25.

The driving part 17 is electrically connected to the control part 25. The driving part 17 deforms the active bending part 21 in a curved shape or a straight state under the control of the control part 25. In the present embodiment, the driving part 17 includes a plurality of actuators, which are not shown, for pulling the angle wire W, which will be described later (see FIG. 2).

The elongated part 20 is coupled to the operation part 2. The elongated part 20 is a rigid tube through which the angle wire W, which will be described later, for bending and deforming the active bending part 21, a signal line to the imaging part 22, or the like is disposed.

The active bending part 21 is coupled to the distal end of the elongated part 20. The active bending part 21 is connected to the driving part 17 by the angle wire W. The active bending part 21 can actively performs a bending operation by the forces by which the driving part 17 pulls the angle wire W. The structure of the active bending part 21 is not particularly limited. For example, the active bending part 21 is formed to have a deformable curved tubular shape as a whole with a plurality of bending pieces, which form a tubular shape, being swingably connected to each other. In this case, the angle wire W is coupled to a bending piece which is located at the most distal side of the plurality of bending pieces.

As shown in FIG. 1, the imaging part 22 is arranged at the distal portion of the elongated part 20, and in the present embodiment, the imaging part 22 is arranged at the distal end 21a of the active bending part 21.

As shown in FIGS. 1 and 3, the imaging part 22 includes an image sensor 22a, an imaging optical system 22b, a slip ring 22c, and a rotation coupling part 23 that rotatably couples the imaging part 22 with the active bending part 21. A commonly known structure, which is capable of capturing an image of an observed object, may be selected appropriately as the configuration of the image sensor 22a and the imaging optical system 22b of the imaging part 22.

The slip ring 22c is disposed in the interior of the imaging part 22. Since the imaging part 22 is electrically connected to the control part 25 via the slip ring 22c, the imaging part 22 can be rotated freely by the rotation coupling part 23.

The rotation coupling part 23 (see FIG. 3) connects the imaging part 22 at the distal end 21a of the active bending part 21. Further, the rotation coupling part 23 is electrically connected to the control part 25. The rotation coupling part 23 rotates the imaging part 22 relative to the active bending part 21 around the optical axis L1 (see FIG. 1) of the imaging part 22 serving as a rotation center, under the control of the control part 25. In order to rotate the imaging part 22 relative to the active bending part 21, for example, an actuator, which is not shown, may be provided at the vicinity of the operation part 2. The position of this actuator is not particularly limited. The imaging part 22 is rotated relative to the active bending part 21, thereby, the rotation coupling part 23 functions as a field-of-view rotating part that rotates the imaging field of view of the imaging part 22 around the optical axis L1 of the imaging part 22 serving as a rotation center. The amount of the rotation by which the rotation coupling part 23 rotates the imaging part 22 under the control of the control part 25 corresponds to the amount of the rotation provided to the control part 25 from the rotation operation input part 4.

The display part 24 is connected to the control part 25. The display part 24 displays an image captured by the imaging part 22. The configuration of the display part 24 is not particularly limited.

As shown in FIGS. 1 and 3, the control part 25 is electrically connected to the driving part 17, the imaging part 22, and the display part 24. As shown in FIG. 3, the control part 25 includes a driving amount calculation part 26, a parameter change part 27, and an image processing part 28.

Information of the moving position of the movable member 12, which is input to the bending operation input part 10, is supplied to the driving amount calculation part 26, thereby, the driving amount calculation part 26 outputs a predetermined driving signal to the driving part 17.

The parameter change part 27 includes a table having a predetermined parameter corresponding to the rotation amount of the rotation cylinder part 5 relative to the base part 3 of the rotation operation input part 4, and an output part that transmits the parameter to the driving amount calculation part 26. Further, the parameter change part 27 receives information of the amount of the relative rotation provided to the control part 25 from the rotation amount detection part 6, and uses the information as the rotation amount of the imaging part 22 relative to the image around the optical axis L1 of the imaging part 22 serving as a rotation center. When there is an input to the rotation operation input part 4, the parameter change part 27 transmits the parameters to the driving amount calculation part 26. The parameter change part 27 changes the bending amount, which is provided from the bending operation input part 10 to the driving amount calculation part 26, in accordance with the rotation amount of the rotation operation input part 4, using the above parameters.

In this way, the control part 25 of the present embodiment specifies a new bending direction of the active bending part 21 so that the bending direction is changed from a direction of the input to the bending operation input part 10 to a direction in which the rotation of the imaging field of view is offset, by changing the bending amount provided from the bending operation input part 10 in accordance with the rotation amount of the rotation operation input part 4. The new bending direction specified by the control part 25 is converted into a signal for driving the driving part 17 to be output to the driving part 17.

The image processing part 28 outputs the image captured by the imaging part 22 to the display part 24. In the present embodiment, the image output from the imaging part 22 to the image processing part 28 is made to be in a state in which the imaging field of view is rotated, by the rotation coupling part 23 which functions as the field-of-view rotating part.

The operation of the endoscope system 1 of the present embodiment will be described.

As shown in FIG. 4, the endoscope system 1 of the present embodiment is introduced into the patient through a small incision formed in a body wall 101 of the patient. Here, the introduction path of the endoscope system 1 into the patient may be a path through the small incision in the body wall 101, or may be a path through a natural orifice such as mouth or the like.

For example, if an observed object 102 (lesion site, or the like) is in the body of the patient, the operator moves the elongated part 20 of the endoscope system 1 so that the observed object 102 is arranged in the imaging field of view of the imaging part 22. The movement of the elongated part 20 of the endoscope system 1 includes an advance or retreat movement in a direction of the longitudinal axis X1 of the elongated part 20, a movement by a pivoting operation of swinging the elongated part 20 with a small incision portion formed in the body wall 101 serving as a fulcrum P, or the like.

If necessary, the operator may bend the active bending part 21 by operating the joystick 13 of the bending operation input part 10. The active bending part 21 is bent and deformed using the joystick 13, thereby, the direction of the imaging field of view of the imaging part 22 can be directed to a direction inclining to the longitudinal axis X1 of the elongated part 20.

When the direction of the imaging field of view of the imaging part 22 is directed to a direction inclining to the longitudinal axis X1 of the elongated part 20, if the elongated part 20 is rotated around the longitudinal axis X1 of the elongated part 20 serving as a rotation center, the imaging part 22 performs a pivoting operation around the longitudinal axis X1 of the elongated part 20 serving as a pivot center. Accordingly, when the direction of the imaging field of view of the imaging part 22 is directed to a direction inclining to the longitudinal axis X1 of the elongated part 20, the imaging part 22 is rotated around the longitudinal axis Y1 of the active bending part 21 or a line parallel to the longitudinal axis Y1 of the active bending part 21 serving as a rotation center, in order to perform an imaging by changing the orientation of the observed object 102 in the imaging field of view of the imaging part 22.

In the present embodiment, by rotating the rotation cylinder part 5 relative to the base part 3 around the center line A1 of the rotation cylinder part 5 serving as a rotation center, the imaging part 22 is rotated with respect to the active bending part 21 at the distal end 21a of the active bending part 21 by the effect of the control part 25 and driving part 17. The rotation center of the imaging part 22 is the optical axis L1 of the imaging part 22.

Although it is not essential to the present invention, the display part 24 displays the image captured by the imaging part 22 so that the optical axis L1 of the imaging part 22 is located at the center of the display area. Therefore, when a region to be observed most desirably is arranged in the center of the display area of the display part 24, the region to be observed most desirably does not easily protrude from the imaging field of view when the imaging part 22 is rotated.

Next, the operation of the endoscope system 1 in a case where the endoscope system 1 is moved relative to the observed object 102 in a state in which the observed object 102 is arranged in the imaging field of view of the imaging part 22 will be described.

In the endoscope system 1 of the present embodiment, the operation of the imaging part 22, which is rotated relative to the active bending part 21 at the distal end 21a of the active bending part 21, is performed under the control of the control part 25 by the operation of rotating the rotation cylinder part 5 relative to the base 3 by the operator. At this time, the rotation of the rotation cylinder part 5 relative to the base part 3 is interlocked with the rotation of the imaging part 22 relative to the active bending part 21, and each rotation angle is equal to each other.

Accordingly, when using the endoscope system 1 of the present embodiment by inserting the elongated part 20 into the body through the abdominal wall of the patient, if a pivoting operation of the elongated part 20 with the abdominal wall of the patient serving as the fulcrum P is performed as shown in FIGS. 4, 5A, 5B, 6A and 6B, the coordinate system in the rotation cylinder part 5 always coincides with the coordinate system of the image.

For example, upward U1, downward D1, left L1, and right R1 in the coordinate system of the rotation cylinder part 5 coincide with upward U2, downward D2, left L2, and right R2 in the image 100 regardless of the rotation state of the imaging part 22. Accordingly, if the rotation cylinder part 5 is moved to upward U1 for example, the imaging part 22 displays the side of downward D2 in the image with the abdominal wall serving as a fulcrum. Such operation is intuitive as the pivoting operation with the abdominal wall serving as a fulcrum. As for downward D1, left L1, and right R1 in the coordinate system of the rotation cylinder part 5, similarly, the movement of the imaging part 22 is performed intuitively as the pivoting operation with the abdominal wall serving as a fulcrum.

Then, in the endoscope system 1 of the present embodiment, when using the endoscope system 1 by inserting the elongated part 20 into the body through the abdominal wall of the patient, upward, downward, left and right (vertical and horizontal) outside of the body do not coincide with upward, downward, left and right in the image. However, upward, downward, left and right in the operation of the joystick 13 in which the direction of the center line A1 of the rotation cylinder part 5 (see FIG. 4) is upward and downward and the circumferential direction A2 of the rotation cylinder part 5 (see FIGS. 5B and 6B) is left and right always coincides with upward, downward, left and right in the image 100.

Accordingly, for the operator who grips the rotation cylinder part 5 and performs an operation of rotating the rotation cylinder part 5 relative to the base part 3, the operation to be performed on the bending operation input part 10 while viewing the image captured by the imaging part 22 is an operation in which the direction of the center line A1 of the rotation cylinder part 5 is upward-downward of the bending and the circumferential direction A2 of the rotation cylinder part 5 is right-left of the bending, regardless of the rotational state of the rotation cylinder part 5.

As described above, in the endoscope system 1, since upward, downward, left and right in the image of the observed object always coincide with upward, downward, left and right in the rotation cylinder part 5, the operation of the active bending part 21 of the endoscope system 1 and the pivoting operation of the elongated part 20 can be performed in the most intuitive positional relationship for the operator to perform the work viewing the display part 24 on which images of the observed object is displayed.

As a result, in the endoscope system 1 of the present embodiment, an intuitive operation feeling is maintained even if the image of the observed object is rotated.

Second Embodiment

Figure 7:
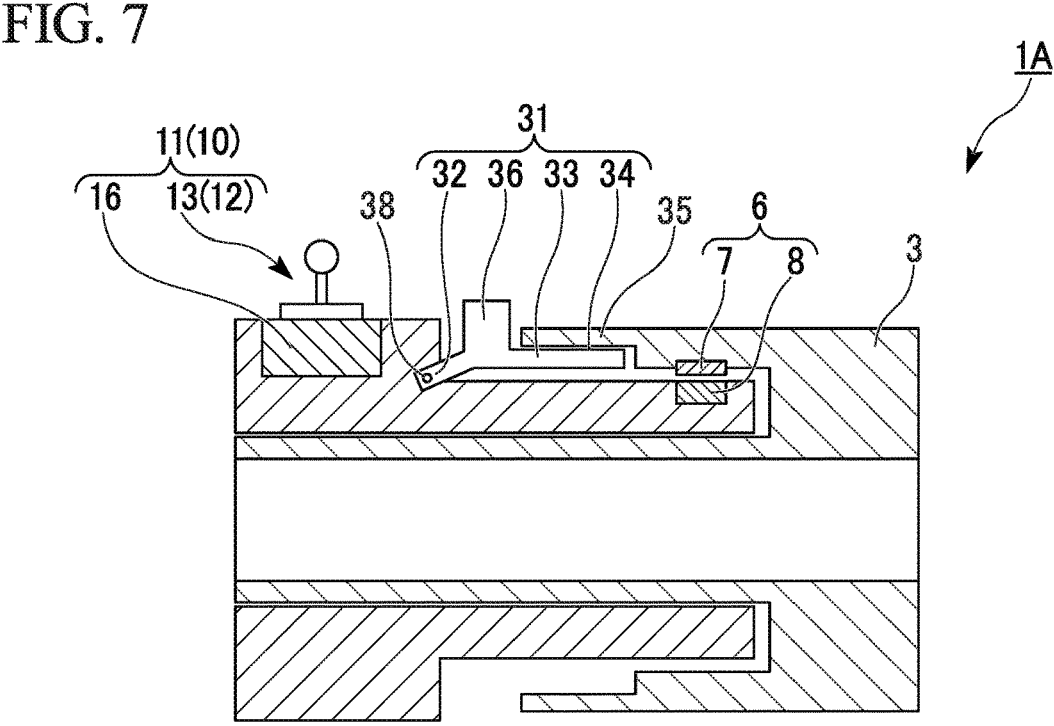
FIG. 7 is a cross sectional view of a part of an operation part of an endoscope system according to a second embodiment of the present invention.
Figure 8:
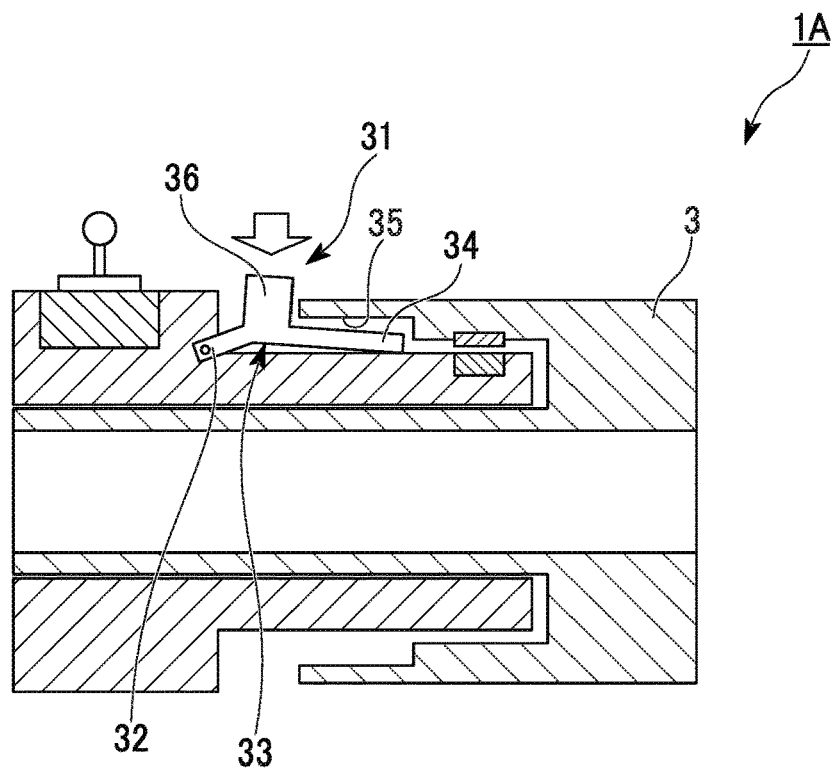
FIG. 8 is a view for describing an operation of the endoscope system.

A second embodiment of the present invention will be described. In each embodiment disclosed below, the same components as disclosed in the above-described first embodiment are denoted by the same reference numerals as in the first embodiment, and a redundant description will be omitted. FIG. 7 is a cross-sectional view of a part of an operation part of the endoscope system of the present embodiment. FIG. 8 is a diagram for describing an operation of the endoscope system.

The endoscope system 1A of the present embodiment shown in FIGS. 7 and 8 is different from that in the first embodiment in that it can be used by switching between a state in which the base part 3 and the rotation cylinder part 5, which are disclosed in the first embodiment, are relatively rotatable, and a state in which the base part 3 and the rotation cylinder part 5 are coupled and relatively non-rotatable.

In the endoscope system 1A of the present embodiment, the operation part 2 disclosed in the first embodiment includes the base part 3 and the rotation cylinder part 5, and further includes a switching part 30 for switching the relative rotation state.

The switching part 30 includes a switch 31, a connecting shaft 38 for connecting the switch 31 to the rotation cylinder part 5, and an engaged part 35 disposed in the base part 3.

The switch 31 includes a fulcrum part 32, an oscillator part 33, and a release button part 36.

The fulcrum part 32 has a through hole through which the connecting shaft 38 is insertable and which are arranged at the end part of the switch 31. The center line of the through hole at the fulcrum part 32 is a center of swinging of the switch 31.

The oscillator part 33 is a rod-like part extending with the fulcrum part 32 serving as an end part. The oscillator part 33 has a contact part 34 contacting to the base part 3. Moreover, the oscillator part 33 has a biasing member, which is not shown, contactable on the outer surface of the rotation cylinder part 5. When the release button part 36 is not pushed, the contact part 34 contacting to the base part 3 can contact with the engaged part 35 of the base part 3.

The contact part 34 contacting to the base part 3 engages frictionally with the engaged part 35 of the base part 3 or meshes with the convex-concave to the engaged part 35 of the base part 3, thereby, the rotation cylinder part 5 contacts to the base part 3 via the switch part 31. In a state in which the contact part 34 contacts to the engaged part 35, the relative rotation of the rotation cylinder part 5 relative to the base part 3 is restricted.

The release button part 36 is a button that can be pushed by the operator in order to separate the contact part 34 provided on the switch 31 from the base part 3. When the release button part 36 is pushed against the urging force of the urging member that urges the oscillator part 33, the switch 31 is moved swinging with the fulcrum part 32 serving as a fulcrum. When the switch 31 swings with the fulcrum part 32 serving as a fulcrum, the contact part 34 provided in the switch 31 is separated away from the engaged part 35 of the base part 3.

The release button part 36 is provided at a boundary part between the base part 3 and the rotation cylinder part 5. In addition, the release button part 36 is arranged on the distal part of the rotation cylinder part 5. For this reason, the release button part 36 is arranged at a position where it is easy for the operator, who grips and operates the rotation cylinder part 5, to push to the release button part 36.

According to the endoscope system 1A of the present embodiment, the switching part 30 switches, by the operation of the switch 31, between a state in which the relative rotation of the rotation operation input part 4 with respect to the elongated part 20 is enabled and a state in which the relative rotation of the rotation operation input part 4 with respect to the elongated part 20 is disabled.

In the present embodiment, when the elongated part 20 is rotated around the longitudinal axis X1 of the elongated part 20 serving as a rotation center, the relative rotation of the rotation operation input part 4 with respect to the elongated part 20 is disabled and the elongated part 20 can be rotated using the rotation operation input part 4. The operation of rotating the elongated part 20 around the longitudinal axis X1 of the elongated part 20 serving as a rotation center is performed when the imaging part 22 disposed at the distal part of the elongated part 20 pivots around the center line of the elongated part 20 serving as a pivot center.

Further, in the present embodiment, when the imaging part 22 is rotated by rotating the rotation cylinder part 5 relative to the base part 3, the relative rotation of the rotation operation input part 4 with respect to the elongated part 20 is enabled and the imaging part 22 can be rotated using the rotation operation input part 4.

Therefore, in the present embodiment, both of the rotation of the elongated part 20 and the rotation of the imaging part 22 can be performed in a state in which the rotation cylinder part 5 is being held. Therefore, it is not necessary to switch the thing to be held by hands when switching between the rotation of the imaging part 22 and the rotating of the elongated part 20 is performed.

Third Embodiment

Figure 9:
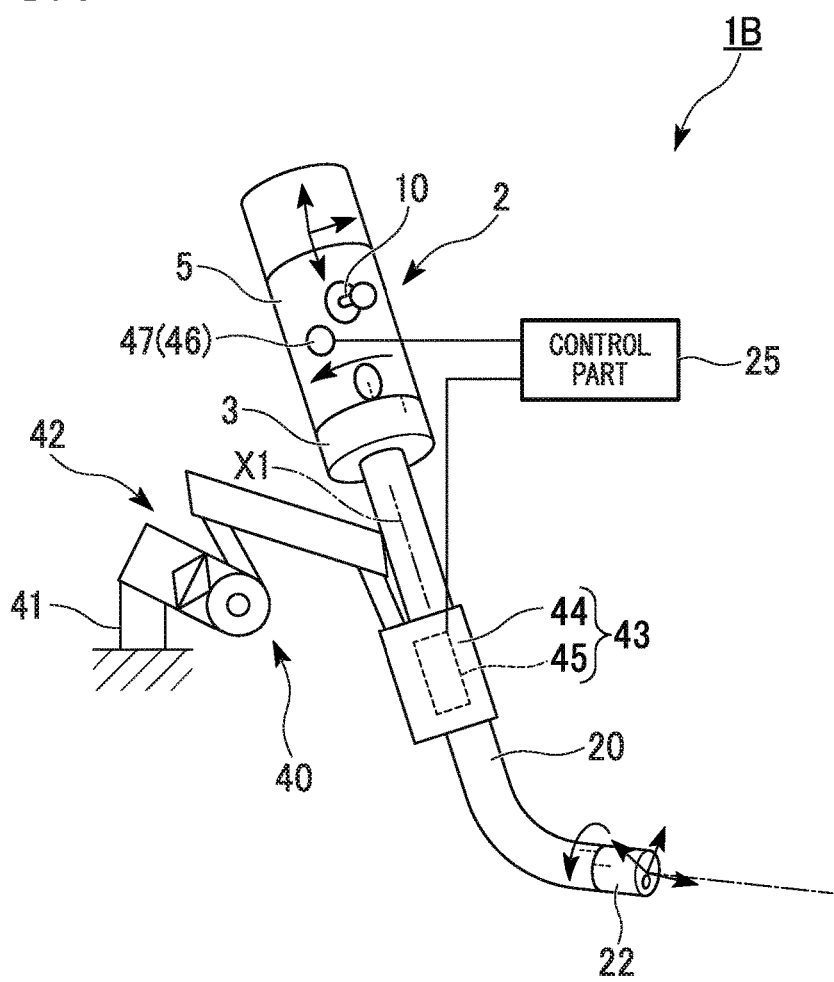
FIG. 9 is a schematic diagram showing a part of an endoscope system according to a third embodiment of the present invention.

A third embodiment of the present invention will be described. FIG. 9 is a schematic view showing a part of an endoscope system of the present embodiment.

As shown in FIG. 9, the endoscope system 1B of the present embodiment is different from the first embodiment in that the endoscope system 1B of the present embodiment further includes a supporting arm 40 that holds the elongated part 20.

The supporting arm 40 includes a base part 41, a movable part 42, and a connecting part 43.

The base part 41 is a part to be fixed to a floor, a desk, or the like.

The movable part 42 includes a plurality of joints that are movably coupled to the base part 41. In the present embodiment, the movable part 42 may be a thing operated on the base part 41 by hand, or one or more joints may be moved by an electrical power. If one or more joints are electrically-powered, the movable part 42 may be a thing operated under the control of the control part 25.

The connecting part 43 includes a holding part 44, a stopper part 45, and a mode change input part 46.

The holding part 44 holds the elongated part 20 so that the elongated part 20 can be rotated relative to the supporting arm 40 around the longitudinal axis X1 of the elongated part 20 serving as a rotation center. For example, the holding part 44 includes a recess to cover the elongated part 20 following the outer peripheral surface of the elongated part 20.

The stopper part 45 restricts the elongated part 20 rotating relative to the supporting arm 40 around the longitudinal axis X1 of the elongated part 20 serving as a rotation center. The configuration of the stopper part 45 is not particularly limited. For example, the stopper part 45 includes a pair of pads that make the elongated part 20 be in a fixed state by contacting with the outer surface of the elongated part 20, and an actuator that switches between fixing and releasing of the elongated part 20 by operating the pair of pads.

The mode change input part 46 includes a push button 47 provided in the operation part 2, so that the operation part 2 performs the fixing and releasing of the elongated part 20 by the stopper part 45

The push button 47 provided in the operation part 2 is connected to the stopper part 45 so as to switch between a mode of fixing the elongated part 20 to the supporting arm 40 by the stopper part 45 and a mode in which the fixing of the elongated part 20 of the supporting arm 40 is released. For example, once the push button 47 provided in the operation part 2 is pushed, the actuator makes the elongated part 20 be in a fixed state, and if the push button 47 provided in the operation part 2 is pushed once more, the actuator makes the fixing the elongated part 20 be released. For example, in the present embodiment, the push button 47 is electrically connected to the actuator of the stopper part 45 via the control part 25.

The position of the push button 47 is preferably located close to the rotation cylinder part 5 or the switch 31 of the operation part 2. If the push button 47 is arranged at a position close to the rotation cylinder part 5 or the switch 31 of the operation part 2, it is easy to operate the push button 47 during the operation using the rotation cylinder part 5.

According to the endoscope system 1B of the present embodiment, the elongated part 20 is supported by the supporting arm 40. When the elongated part 20 is made to be in a fixed state in which the elongated part 20 is fixed to the holding part 44 of the supporting arm 40, it is possible to easily rotate the rotation cylinder part 5 relative to the base part 3 without supporting the base part 3 by the operator. In addition, the fixing and releasing of the elongated part 20 to/from the holding part 44 of the supporting arm 40 can be easily manipulated by the push button 47.

Here, if the push button 47 is arranged at a position where the operator of the endoscope system 1B can easily push the push button 47 during the operation of switching between the rotation of the elongated part 20 and the rotation of the imaging part 22, it is not essential that the operation part 2 is provided. For example, the push button 47 may be arranged on a floor as a foot switch.

Fourth Embodiment

Figure 10:
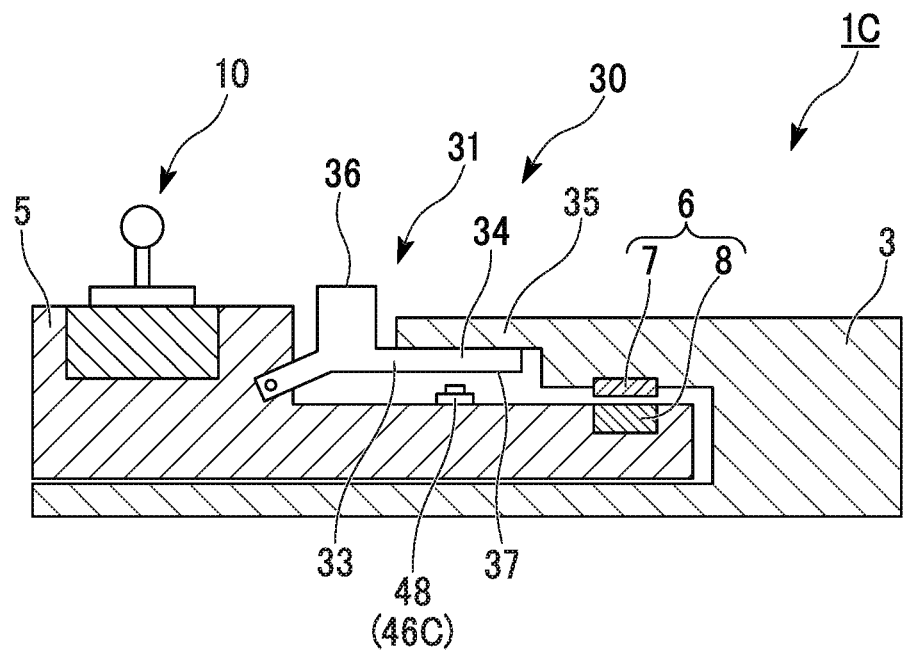
FIG. 10 is a cross sectional view of a part of an operation part of an endoscope system according to a fourth embodiment of the present invention.
Figure 11:
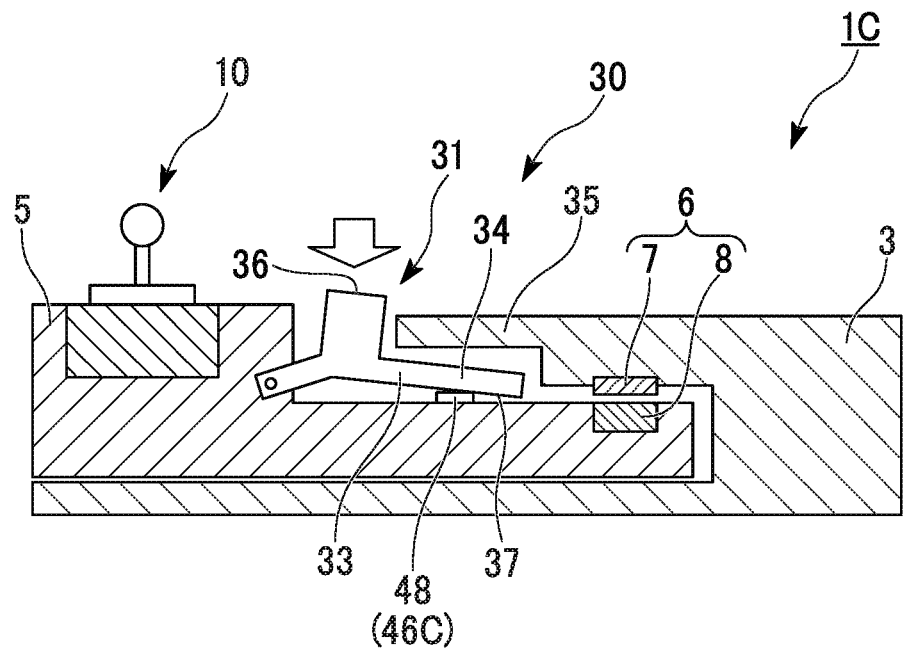
FIG. 11 is a diagram for describing an operation of the endoscope system.

A fourth embodiment of the present invention will be described. FIG. 10 is a cross-sectional view of a part of an operation part of the endoscope system of the present embodiment. FIG. 11 is a diagram for describing the operation of the endoscope system.

As shown in FIG. 10, the endoscope system 1C of the present embodiment is different from the above third embodiment in that the mode change input part 46 disclosed by the above third embodiment operates in conjunction with the operation for the release button part 36 disclosed in the second embodiment.

In the endoscope system 1C of the present embodiment, the switching part 30 disclosed by the second embodiment further includes a mode change input part 46C that performs a switching operation by the switch 31 of the operation part 2. In the present embodiment, the push button 47 disclosed by the above third embodiment is not provided in the endoscope system 1C.

The mode change input part 46C of the present embodiment includes a contact point part 48 that is electrically connected to the supporting arm 40 via the control part 25.

In the present embodiment, the oscillator part 33 of the switch 31 of the operation part 2 further includes a pressing part 37 facing the contact point part 48 at a part of a surface located at opposite side of the contact part 34 facing the base part 3.

As shown in FIG. 11, in the endoscope system 1C of the present embodiment, when the pressing part 37 presses the contact point part 48, the stopper part 45 makes the elongated part 20 to be in a fixed state relative to the holding part 44. In the endoscope system 1C of the present embodiment, when the pressing part 37 is separated from the contact point part 48, the fixed state of the elongated part 20 by the stopper part 45 relative to the holding part 44 is released.

According to the endoscope system 1C of the present embodiment, the rotation of the rotation cylinder part 5 relative to the base part 3 becomes possible by pushing the release button part 36, and the elongated part 20 is fixed by the stopper part 45 so that a rotation of the elongated part 20 relative to the holding part 44 around the longitudinal axis X1 of the elongated part 20 serving as a rotation center does not occur. Therefore, when the release button part 36 is pushed, it is possible to easily rotate the rotation cylinder part 5 relative to the base part 3.

According to the endoscope system 1C of the present embodiment, it is impossible to rotate the rotation cylinder part 5 relative to the base part 3 in a state in which the release button part 36 is not pushed, and the elongated part 20 is rotated freely relative to the holding part 44 around the longitudinal axis X1 of the elongated part 20 serving as a rotation center.

Thus, in the present embodiment, in a state in which the elongated part 20 is being held by the supporting arm 40, it is possible to easily switch between a rotation of the imaging part 22 by rotating the rotation cylinder part 5 relative to the base part 3 and a rotation of the elongated part 20 by rotating the rotation cylinder part 5 together with the base part 3, and perform the switched rotation.

Fifth Embodiment

Figure 12:
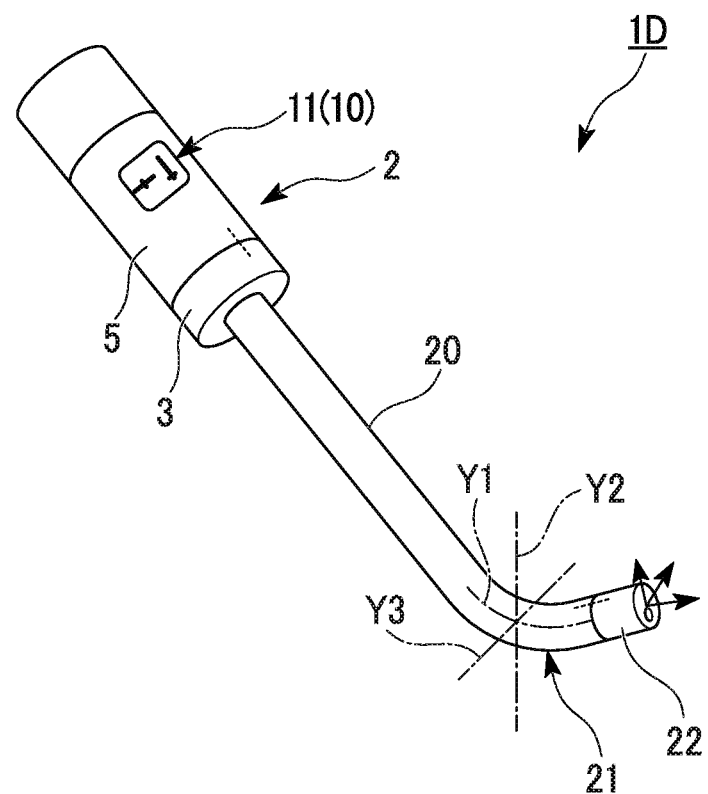
FIG. 12 is a schematic diagram showing a part of an endoscope system according to a fifth embodiment of the present invention.
Figure 13:
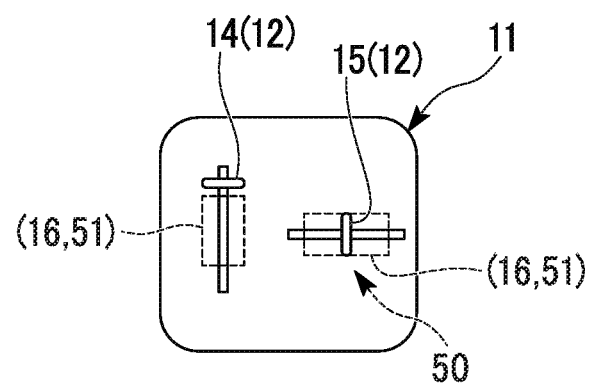
FIG. 13 is a schematic diagram for describing a configuration of an input device and a feedback mechanism of the endoscope system.
Figure 14:
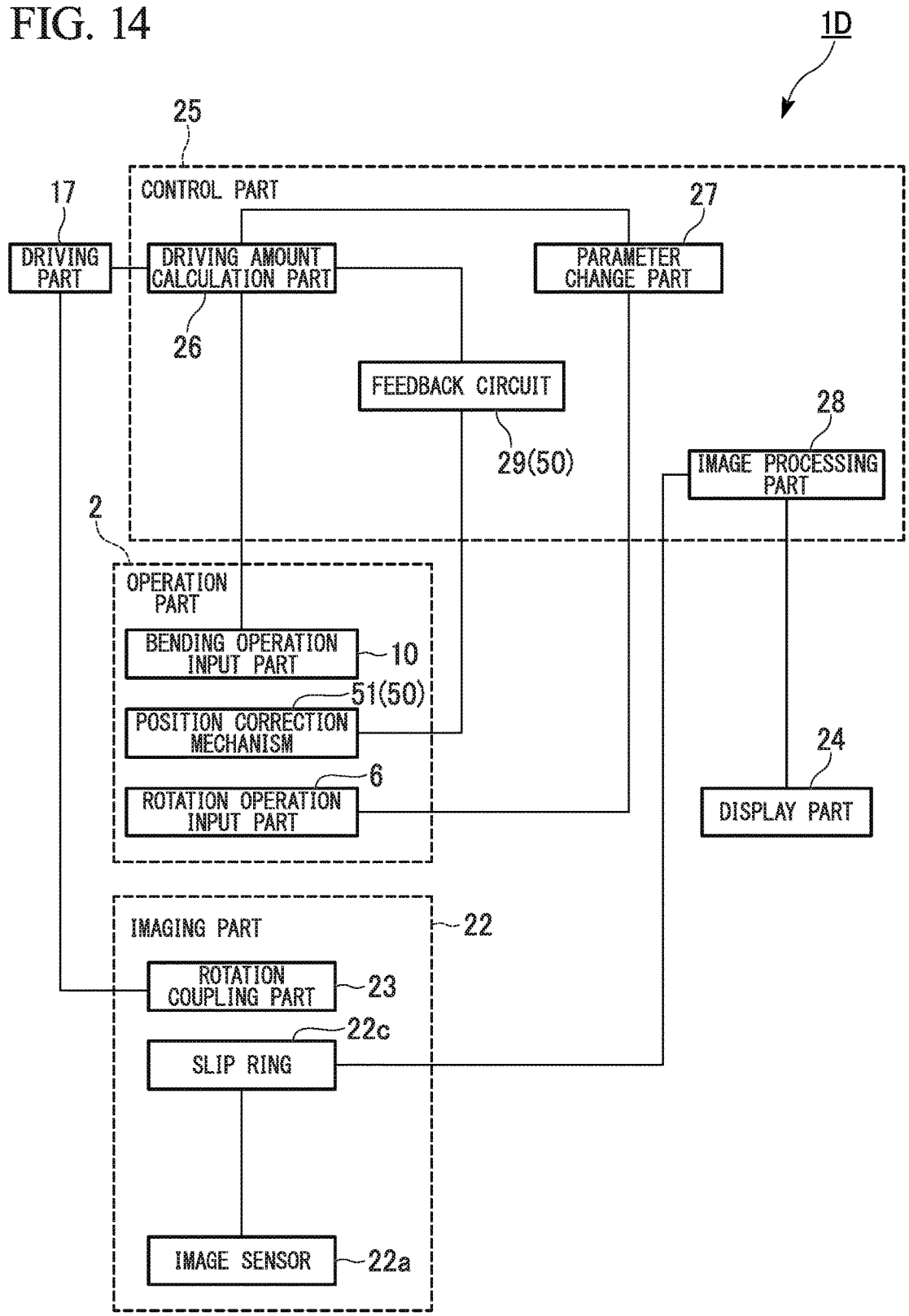
FIG. 14 is a block diagram of the endoscope system.

A fifth embodiment of the present invention will be described. FIG. 12 is a schematic diagram showing a part of an endoscope system of the present embodiment. FIG. 13 is a schematic diagram for describing a configuration of an input device and feedback mechanisms of the endoscope system. FIG. 14 is a block diagram of the endoscope system.

As shown in FIGS. 12 and 14, in the endoscope system 1D of the present embodiment, the bending operation input part 10 disclosed by the first embodiment further includes a position correction mechanism 51 for moving the movable member 12 disclosed by the first embodiment.

The position correction mechanism 51 is connected to the movable member 12. The position correction mechanism 51 includes an actuator, which is not shown, for moving the movable member 12 under the control of a feedback circuit 29, which will be described later. In the position correction mechanism 51, a first lever 14 and a second lever 15, which correspond to the movable member 12 of the present embodiment, can be moved independently.

The input device 11 of the bending operation input part 10 of the present embodiment includes the first lever 14 and the second lever 15 as the movable member 12 disposed in the rotation operation input part 4, instead of the joystick 13 of the first embodiment.

The first lever 14 is a lever for bending the active bending part 21 in the straight direction Y2 (for example, upward-downward direction) perpendicular to the longitudinal axis Y1 of the active bending part 21. In the present embodiment, the first lever 14 bends the active bending part 21 in the upward-downward direction of the image displayed on the display part 24.

The second lever 15 is a lever for bending the active bending part 21 in the straight Y3 direction (for example, left-right direction) orthogonal to both of the longitudinal axis Y1 of the active bending part 21 and the above straight line Y2. In the present embodiment, the second lever 15 bends the active bending part 21 in the left-right direction of the image displayed on the display part 24.

In the encoder 16 of the present embodiment, moving amounts or positions of the first lever 14 and the second lever 15 of the bending operation input part 10 are detected and output to the control part 25. That is, the encoder 16 outputs the bending amount (control target value) of the active bending part 21, which is input to each of the first lever 14 and the second lever 15, to the control part 25.

Further, in the present embodiment, the control part 25 disclosed by the first embodiment includes the driving amount calculation part 26, the parameter change part 27, and the image processing part 28, which are disclosed by the first embodiment, and further includes a feedback circuit 29.

As shown in FIG. 14, the feedback circuit 29 associates upward and downward in the image with the position of the first lever 14 and associates left and right in the image with the position of the second lever 15, in response to the change in the positional relationship in the image caused in accordance with the rotation amount with respect to the base part 3 of the rotation cylinder part 5 of the rotation operation input part 4. Furthermore, the feedback circuit 29 moves the first lever 14 and the second lever 15 by operating the position correction mechanism 51 so that the bending state of the active bending part 21 can be indicated based on upward, downward, left and right in the image.

As a simple specific example, in the present embodiment, when the active bending part 21 is bent to upward direction (upward direction in the upward-downward direction of the image displayed on the display part 24) using the first lever 14 of the input device 11 for example, the first lever 14 is in a position shifted from the neutral position and the second lever is in the neutral position.

If the imaging part 22 is rotated by 90 degrees around its optical axis L1 serving as a rotation center without changing the bending state of the active bending part 21, the absolute position of the active bending part 21 is not changed and the relative positional relationship of the active bending part 21 with respect to the imaging part 22 is changed by 90 degrees, therefore, the active bending part 21 is being bent in left-right direction when viewed relative to upward, downward, left and right in the image displayed on the display part 24 serving as a standard.

In this case, in the present embodiment, the feedback circuit 29 recognizes that the imaging part 22 is rotated by 90 degrees since the rotation cylinder part 5 is rotated by 90 degrees with respect to the base part 3, and returns the first lever 14 to the neutral position and moves the second lever from the neutral position. Thereby, the position of the movable member 12 in the input device 11 is changed from a position, which indicates that the active bending part 21 is facing to upward direction, to a position which indicates that the active bending part 21 is facing to left-right direction.

In the present embodiment, by the position correction mechanism 51 and the feedback circuit 29, a feedback mechanism 50, which performs a feedback to the movable member 12, is configured so as to indicate the bending state of the active bending part 21 relative to upward, downward, left and right in the image serving as a standard. The feedback mechanism 50 performs a feedback to the movable member 12 when there is an input for rotation to the rotation operation input part 4.

According to the endoscope system 1D of the present embodiment, the deviation from the direction of the input to the input device 11 caused by the rotation amount of the rotation operation input part 4 is fed back to the input device 11 by the feedback mechanism 50, thereby, the relationship between upward, downward, left and right in the image and upward, downward, left and right of the movable member 12 is maintained even if there is an input to the rotation operation input part 4. Therefore, according to the endoscope system 1D of the present embodiment, it is possible to intuitively operate the input device 11 based on upward, downward, left and right in the image.

While the embodiments of the present invention have been described in detail with reference to the drawings, specific configurations are not limited to these embodiments, and design modifications or the like without departing from the scope of the present invention are also included.

For example, instead of the movable member 12 disclosed by the first embodiment and the fifth embodiment, a touch panel for outputting the bending amount of the active bending part 21 may be included. In this case, the feedback mechanism 50 disclosed by the fifth embodiment performs a feedback by changing the display state of the touch panel, thereby, the same effect as in the fifth embodiment can be attained.

Further, in the above embodiments, although an example in which the image of the observed object is rotated by rotating the imaging part 22 relative to the active bending part 21 is disclosed, the rotation of the image of the observed object may be performed not by the rotation of the imaging part 22 but by the image processing performed on the image captured by the imaging part 22. In this case, it is not necessary to physically rotate the imaging part 22 relative to active bending part 21, and the rotation coupling part 23 and the slip ring 22c, which are disclosed by the above embodiments, become unnecessary.

For example, in the first embodiment, without being provided with a rotation coupling part 23 and the slip rings 22c, the image processing part 28 may become the field-of-view rotating part and rotate the image from the imaging part 22 by a coordinate conversion or the like to output to the display part 24.

Moreover, the pivoting operation in which the fulcrum P of the endoscope system 1 disclosed by the first embodiment is serving as a swing center has the same effect even if the active bending part 21 is not included in the endoscope system 1. As an example, a configuration can be cited in which the imaging part is rotated relative to the distal end of the tube that is being bent to have a predetermined bending shape instead of actively bending for example.

Moreover, in the above embodiments, an example in which the imaging part is electrically connected to the control part is disclosed, but the connection mode between the imaging part and the control part is not limited as long as transmission of the image signal is possible, and may be a wireless connection, a wired connection, or the like.

Moreover, in the above embodiments, while an example in which the operation part is connected to the driving part is disclosed, the driving part may be included inside the operation part and the driving signal from the control part may be output to the driving part in the operation part.

Moreover, in the above embodiments, while an example in which the elongated part 20 is rigid is shown, the elongated part 20 may have flexibility over a part of it or the whole area.

Moreover, the active bending part disclosed in the above embodiments may have a bending configuration capable of being bent in one direction, that is, being bent only in upward, downward, left and right direction.

Moreover, the components shown in each embodiment and the technical matters disclosed by the above as design changes to the components can be constituted by being combined as appropriate.

What is claimed is:

1. An endoscope system comprising:
   an operation part;
   an elongated part configured to rotate relative to the operation part around a longitudinal axis of the elongated part, wherein a distal part of the elongated part is configured to be actively bent by a bending force generated by a first actuator;
   an image sensor arranged in the distal part of the elongated part, wherein the image sensor has an optical axis, and wherein the image sensor is configured to capture an image of an object within a field of view of the image sensor;
   a sensor configured to detect an amount of rotation of the elongated part around the longitudinal axis; and
   a controller configured to:

receive an instruction to bend the distal part of the elongated part in a first direction;
control the first actuator to generate the bending force to bend the distal part of the elongated part in the first direction; and
when the distal part of the elongated part has been bent in the first direction,
receive the amount of rotation of the elongated part around the longitudinal axis detected by the sensor;
determine a second direction to bend the distal part of the elongated part in accordance with the amount of rotation of the elongated part around the longitudinal axis detected by the sensor to offset a rotation of the field of view of the image sensor caused by rotation of the elongated part around the longitudinal axis of the elongated part; and
control the first actuator to generate the bending force to bend the distal part of the elongated part in the second direction.

2. The endoscope system according to claim 1, further comprising:
a switch configured to switch the elongated part between a state in which it is possible for the elongated part to rotate relative to the operation part, and a state in which it is impossible for the elongated part to rotate relative to the operation part.

3. The endoscope system according to claim 1, further comprising:
a supporting arm configured to hold the elongated part; and
a switch configured to switch the elongated part between a mode in which it is possible for the elongated part to rotate relative to the supporting arm, and a mode in which it is impossible for the elongated part to rotate relative to the supporting arm.

4. The endoscope system according to claim 1, further comprising:
an input device configured to receive an operation corresponding to the instruction to bend the distal part of the elongated part in the first direction; and
a feedback mechanism configured to provide feedback to the input device wherein the feedback corresponds to a deviation from the first direction caused in accordance with the amount of rotation.

5. The endoscope system according to claim 1, further comprising:
a second actuator arranged in the elongated part, wherein the second actuator is configured to be controlled to rotate the image sensor around the optical axis of the image sensor,
wherein the controller is configured to control the second actuator to rotate the image sensor around the optical axis of the image sensor in accordance with the amount of rotation of the elongated part around the longitudinal axis detected by the sensor.

6. The endoscope system according to claim 1,
wherein the controller is configured to rotate the image captured by the image sensor in accordance with the amount of rotation of the elongated part around the longitudinal axis detected by the sensor.

7. An endoscope system comprising:
an operation part;
an elongated part configured to rotate relative to the operation part around a longitudinal axis of the elongated part, wherein a distal part of the elongated part is configured to be actively bent by a bending force generated by a first actuator;
an image sensor arranged in the distal part of the elongated part, wherein the image sensor has an optical axis, and wherein the image sensor is configured to capture an image of an object within a field of view of the image sensor;
a second actuator arranged in the elongated part, wherein the second actuator is configured to be controlled to rotate the image sensor around the optical axis of the image sensor;
a sensor configured to detect an amount of rotation of the elongated part around the longitudinal axis; and
a controller configured to:
receive an instruction to bend the distal part of the elongated part in a first direction;
control the first actuator to generate the bending force to bend the distal part of the elongated part in the first direction;
when the distal part of the elongated part has been bent in the first direction,
receive the amount of rotation of the elongated part around the longitudinal axis detected by the sensor;
determine a second direction to bend the distal part of the elongated part in accordance with the amount of rotation of the elongated part around the longitudinal axis detected by the sensor to offset a rotation of the field of view of the image sensor caused by rotation of the elongated part around the longitudinal axis of the elongated part; and
control the first actuator to generate the bending force to bend the distal part of the elongated part in the second direction; and
control the second actuator to rotate the image sensor around the optical axis of the image sensor based on the amount of rotation of the elongated part around the longitudinal axis detected by the sensor.

8. An endoscope system comprising:
an operation part;
an elongated part configured to rotate relative to the operation part around a longitudinal axis of the elongated part, wherein a distal part of the elongated part is configured to be actively bent by a bending force generated by an actuator;
an image sensor arranged in the distal part of the elongated part, wherein the image sensor has an optical axis, and wherein the image sensor is configured to capture an image of an object within a field of view of the image sensor;
a sensor configured to detect an amount of rotation of the elongated part around the longitudinal axis; and
a controller configured to:
receive an instruction to bend the distal part of the elongated part in a first direction;
control the actuator to generate the bending force to bend the distal part of the elongated part in the first direction;
when the distal part of the elongated part has been bent in the first direction,
receive the amount of rotation of the elongated part around the longitudinal axis detected by the sensor;
determine a second direction to bend the distal part of the elongated part in accordance with the amount of rotation of the elongated part around the longitudinal axis detected by the sensor to offset a rotation of the field of view of the image sensor caused by rotation of the elongated part around the longitudinal axis of the elongated part; and control the actuator to generate the bending force to bend the distal part of the elongated part in the second direction; and rotate the image captured by the image sensor in accordance with the amount of rotation of the elongated part around the longitudinal axis detected by the sensor.

* * * * *